(12) United States Patent
Hasegawa et al.

(10) Patent No.: US 8,975,385 B2
(45) Date of Patent: Mar. 10, 2015

(54) RARE-EARTH COMPLEX AND USES THEREOF

(75) Inventors: Yasuchika Hasegawa, Ikoma (JP); Tsuyoshi Kawai, Ikoma (JP); Takuya Nakashima, Ikoma (JP); Tetsuya Nakagawa, Ikoma (JP); Kohei Miyata, Ikoma (JP)

(73) Assignee: National University Corporation Nara Institute of Science and Technology, Nara (JP)

( * ) Notice: Subject to any disclaimer, the term of this patent is extended or adjusted under 35 U.S.C. 154(b) by 444 days.

(21) Appl. No.: 13/387,013

(22) PCT Filed: Jul. 15, 2010

(86) PCT No.: PCT/JP2010/061960
§ 371 (c)(1),
(2), (4) Date: Feb. 22, 2012

(87) PCT Pub. No.: WO2011/013520
PCT Pub. Date: Feb. 3, 2011

(65) Prior Publication Data
US 2012/0140439 A1   Jun. 7, 2012

(30) Foreign Application Priority Data

Jul. 29, 2009 (JP) ................................ 2009-176558

(51) Int. Cl.
| | | |
|---|---|---|
| *C07F 5/00* | (2006.01) | |
| *F21V 9/16* | (2006.01) | |
| *C07F 9/53* | (2006.01) | |
| *C07F 9/572* | (2006.01) | |
| *C07F 9/58* | (2006.01) | |
| *C07F 9/655* | (2006.01) | |
| *C09K 11/06* | (2006.01) | |
| *H01L 51/00* | (2006.01) | |
| *H05B 33/14* | (2006.01) | |
| *H01L 51/50* | (2006.01) | |

(52) U.S. Cl.
CPC ............ *C07F 9/5329* (2013.01); *C07F 9/5345* (2013.01); *C07F 9/5723* (2013.01); *C07F 9/582* (2013.01); *C07F 9/65515* (2013.01); *C07F 9/65522* (2013.01); *C07F 9/65527* (2013.01); *C09K 11/06* (2013.01); *C09K 2211/1007* (2013.01); *C09K 2211/1088* (2013.01); *C09K 2211/182* (2013.01); *H01L 51/0089* (2013.01); *H01L 51/5016* (2013.01); *H05B 33/14* (2013.01); *C07F 5/003* (2013.01)
USPC ............................................. 534/15; 362/84

(58) Field of Classification Search
CPC  H01L 51/0089; H01L 51/5016; H05B 33/14; C07F 9/5345; C07F 5/003; C07F 9/5723; C07F 9/5329; C07F 9/582; C07F 9/65515;
C07F 9/65522; C07F 9/65527; A61K 49/0013; A61K 49/0017; A61K 49/0019; C09K 11/06; C09K 2211/1007; C09K 2211/1088; C09K 2211/182
USPC ...................... 424/9.6, 9.361; 362/84; 534/15
See application file for complete search history.

(56) References Cited

U.S. PATENT DOCUMENTS

| | | | |
|---|---|---|---|
| 6,300,481 | B1 | 10/2001 | Yanagida et al. |
| 2008/0171858 | A1 | 7/2008 | Nagata et al. |
| 2008/0303426 | A1 | 12/2008 | Iwanaga et al. |

FOREIGN PATENT DOCUMENTS

| | | | |
|---|---|---|---|
| CN | 1687080 | * 10/2005 | ............... C07F 5/00 |
| CN | 1749352 | 3/2006 | |
| JP | 2000-63682 | 2/2000 | |
| JP | 2003-81986 | 3/2003 | |
| JP | 2004-262909 | 9/2004 | |
| JP | 2005-97240 | 4/2005 | |
| JP | 2007-210945 | 8/2007 | |
| JP | 2008-31120 | 2/2008 | |
| JP | 2008-297250 | 12/2008 | |
| WO | 98/40388 | 9/1998 | |

OTHER PUBLICATIONS

Raj, D. et al., Dalton Transactions, 2009, p. 7519-7528.*
Nakamura, K., et al., "Enhanced Lasing Properties of Dissymmetric Eu (III) Complex with Bidentate Phosphine Ligands," J. Phys. Chem. A 2007, 3029-3037.
Xu, Hui, et al., Bright electroluminescence from a chelate phosphine oxide EuIII complex with high thermal performance, Thin Solid Films, 2008, vol. 516, No. 23, p. 8487-8492.

(Continued)

*Primary Examiner* — Michael G Hartley
*Assistant Examiner* — Leah Schlientz
(74) *Attorney, Agent, or Firm* — Kagan Binder, PLLC (57) ABSTRACT

The rare-earth complex of the present invention has high luminous efficiency, since it has a structure represented by the following general formula (I):

Chem. 1

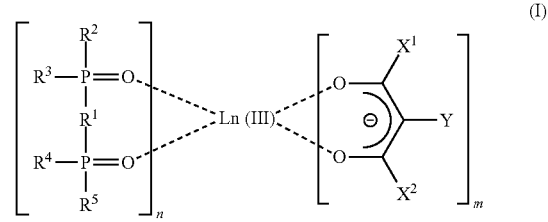

4 Claims, 1 Drawing Sheet

(56) References Cited

OTHER PUBLICATIONS

PCT International Search Report in International Application No. PCT/JP2010/061960, mailed Sep. 21, 2010, with English translation, 4 pgs.

Moudam et al., "Europium complexes with high total photoluminescence quantum yields in solution and in PMMA," Chem. Commun., No. 43, 6649-6651, Sep. 25, 2009.

Second Office Action for corresponding JP Patent Application No. 2011-524734, mailed May 27, 2014.

Fawcett et al., "Lanthanide halide and nitrate complexes with potentially tridentate bisphosphine dioxide—either donors," Polyhedron, 2004, vol. 23, p. 2561-2567.

Second Office Action for corresponding EP Patent Application No. 10804266.4, Apr. 30, 2014.

Kawai et al., "Emission properties of Sm(III) complexes having remarkably deep-red emission band," Journal of Alloys and Compounds, 488 (2009) 612-614.

* cited by examiner

RARE-EARTH COMPLEX AND USES THEREOF

TECHNICAL FIELD

The present invention relates to a rare-earth complex having emission properties, and uses thereof.

BACKGROUND ART

It is known that there are some rare earth ions which emit light of a broad wavelength area, in a range from ultraviolet to infrared rays. This emission of light is based on electron transition derived from an f orbit which cannot be easily affected by the external field, such as a ligand field. Therefore, a wavelength interval of an emission band is extremely narrow as compared to that of an organic fluorescent substance and like substance, and color purity is theoretically high. The rare earth ion compares favorably with an organic fluorescent substance, in terms of heat, light, and stability over excitation. Furthermore, the rare earth ion is nonpoisonous, and therefore can be used easily industrially.

Since the rare earth ion has excellent characteristics as such, a rare-earth complex in which various ligands are coordinated to a rare earth ion are used for various purposes. More specifically, the rare-earth complex is used for various uses such as luminous ink and organic electroluminescence elements.

In order to enable application of the rare earth ion having such an excellent characteristic in further various fields, various researches have been performed regarding the rare earth ion and the rare-earth complex.

For example, the inventors of the present invention have developed several rare-earth complexes until now (for example, see Patent Literatures 1 to 4, and Non Patent Literature 1).

CITATION LIST

Patent Literature

Patent Literature 1
International Publication WO98/40388 (International Publication Date Sep. 17, 1998)
Patent Literature 2
Japanese Patent Application Publication, Tokukai, No. 2000-63682 A (Publication Date: Feb. 29, 2000)
Patent Literature 3
Japanese Patent Application Publication, Tokukai, No. 2003-81986 A (Publication Date: Mar. 19, 2003)
Patent Literature 4
Japanese Patent Application Publication, Tokukai, No. 2008-31120 A (Publication Date: Feb. 14, 2008)

Non Patent Literature

Non Patent Literature 1
Nakamura K. et al., J. Phys. Chem. A, Vol. 111, No. 16, 3029-3037 (2007).

SUMMARY OF INVENTION

Technical Problem

Although various rare-earth complexes have been developed until now as described above, there are still few rare-earth complexes which have high luminous efficiency. For this reason, in order to use the rare-earth complex for broader uses, more kinds of rare-earth complexes which have a high luminous efficiency are in demand.

The present invention is accomplished in view of the foregoing problem, and an object thereof is to provide a rare-earth complex having a high luminous efficiency.

Solution to Problem

In order to attain the object, a rare-earth complex according to the present invention is a rare-earth complex represented by the following general formula (I):

Chem. 1 wherein

Ln is a rare earth atom, and $R^1$ is $-A^1-$, $-B^1-A^2-B^2-$, $-A^3-B^3-A^4-$, $-A^5-B^4-A^6-B^5-A^7-$ or Chem. 2

$A^1$ being an alicyclic hydrocarbon group, an aromatic hydrocarbon group having a condensed polycyclic structure, a heterocyclic group, or an alkenylene group or an alkynylene group having a straight chain or a branched chain and having at least one unsaturated bond in a carbon chain that links together carbon atoms having a free valence, $A^2$, $A^3$, $A^4$, $A^5$, $A^6$, $A^7$, $A^8$, and $A^9$ each independently being an alicyclic hydrocarbon group, an aromatic hydrocarbon group, a heterocyclic group, or an alkenylene group or alkynylene group having a straight chain or a branched chain and having at least one unsaturated bond in a carbon chain that links together carbon atoms having a free valence, $B^1$, $B^2$, $B^3$, $B^4$, and $B^5$ each independently being an alkylene group, an alkynylene group, or —O—, the alkylene group or alkynylene group having a straight chain or a branched chain and which may contain at least one atom selected from the group consisting of O and N, $R^2$, $R^3$, $R^4$, and $R^5$ each independently being an alkyl group, alkenyl group or alkynyl group each having a straight chain or a branched chain, or alternatively an alicyclic hydrocarbon group, an aromatic hydrocarbon group, a heterocyclic group, or alternatively a halogen group, a hydroxyl group, a sulfonic group, a carbonyl group, a nitro group, a cyano group, or an amino group, two adjacent ones of $R^2$, $R^3$, $R^4$, and $R^5$ may together form a ring structure, $X^1$ and $X^2$ each independently being an alkyl group having a straight chain or a branched chain, an alicyclic hydrocarbon group, an aromatic hydrocarbon group, a heterocyclic group, or a group made up of a straight chain or a branched chain including no hydrogen atom, Y being hydrogen, heavy hydrogen, a halogen group, a hydroxyl group, a sulfonic group, a carbonyl group, a nitro group, a cyano group, an amino group, an alkyl group having a straight chain or a branched chain, or alternatively an alicyclic hydrocarbon group, an aromatic hydrocarbon group, a heterocyclic group, or a group made of a straight chain or a branched chain including no hydrogen atom, and n being 1 or 2; m being 2, 3, or 4; and p and q each independently being an integer from 2 to 10.

Since the rare-earth complex according to the present invention has the foregoing structure, the light energy that excites the rare earth ion is not easily released as thermal energy. As a result, the rare earth ion is sufficiently excited, thereby showing high luminous efficiency.

That is, in the foregoing structure, a phosphine oxide bidentate ligand (n number of ligand(s) coordinated to Ln(III) in general formula (I)) includes two or more bonds (for example, an unsaturated bond, an arylene group) in a joint part in which two P atoms are linked together. For this reason, it is assumed that a change in the configuration in the phosphine oxide bidentate ligand is restricted, thereby contributing to the emission properties. The idea that luminous efficiency improves by controlling a change in configuration is not known until now.

The luminous material according to the present invention includes the rare-earth complex according to the present invention described above.

According to the arrangement, since the rare-earth complex according to the present invention demonstrates outstanding emission properties, it is possible to provide a luminous material which can be suitably used for luminous ink or organic electroluminescence elements.

A light emitting device according to the present invention includes: a light source; and the luminous material according to the present invention.

According to the arrangement, the rare-earth complex according to the present invention demonstrates outstanding emission properties. Hence, it is possible to provide a light emitting device which demonstrates outstanding emission properties.

Advantageous Effects of Invention

As described above, the rare-earth complex according to the present invention has a structure represented by general formula (I). Hence, the rare-earth complex has a high luminous efficiency.

BRIEF DESCRIPTION OF DRAWINGS

FIG. 1

FIG. 2

DESCRIPTION OF EMBODIMENTS

[I] Rare-Earth Complex

A rare-earth complex according to the present embodiment is represented by the following general formula (I):

Chem. 3

(I)

where Ln is a rare earth atom, and
$R^1$ is -$A^1$-, -$B^1$-$A^2$-$B^2$-, -$A^3$-$B^3$-$A^4$-, -$A^5$-$B^4$-$A^6$-$B^5$-$A^7$-, or Chem. 4 where
$A^1$ is an alicyclic hydrocarbon group, an aromatic hydrocarbon group having a condensed polycyclic structure, a heterocyclic group, or an alkenylene group or an alkynylene group having a straight chain or a branched chain and having at least one unsaturated bond in a carbon chain that links together carbon atoms having a free valence, $A^2$, $A^3$, $A^4$, $A^5$, $A^6$, $A^7$, $A^8$, and $A^9$ are each independently an alicyclic hydrocarbon group, an aromatic hydrocarbon group, a heterocyclic group, or an alkenylene group or alkynylene group having a straight chain or a branched chain and having at least one unsaturated bond in a carbon chain that links together carbon atoms having a free valence, $B^1$, $B^2$, $B^3$, $B^4$, and $B^5$ are each independently an alkylene group, an alkynylene group, or —O—, the alkylene group or alkynylene group having a straight chain or a branched chain and which may contain at least one atom selected from the group consisting of O and N, $R^2$, $R^3$, $R^4$, and $R^5$ are each independently an alkyl group, alkenyl group or alkynyl group each having a straight chain or a branched chain, or alternatively, an alicyclic hydrocarbon group, an aromatic hydrocarbon group, a heterocyclic group, or alternatively a halogen group, a hydroxyl group, a sulfonic group, a carbonyl group, a nitro group, a cyano group, or an amino group, two adjacent ones of $R^2$, $R^3$, $R^4$, and $R^5$ may together form a ring structure, $X^1$ and $X^2$ are each independently an alkyl group having a straight chain or a branched chain, an alicyclic hydrocarbon group, an aromatic hydrocarbon group, a heterocyclic group, or a group made up of a straight chain or a branched chain including no hydrogen atom, Y is hydrogen, heavy hydrogen, a halogen group, a hydroxyl group, a sulfonic group, a carbonyl group, a nitro group, a cyano group, an amino group, an alkyl group having a straight chain or a branched chain, or alternatively, an alicyclic hydrocarbon group, an aromatic hydrocarbon group, a heterocyclic group, or a group made of a straight chain or a branched chain including no hydrogen atom, and n is 1 or 2; m is 2, 3, or 4; and p and q are each independently an integer from 2 to 10.

The rare-earth complex, having the foregoing structure, has a high quantum yield and shows a sharp emission spectrum. Accordingly, the rare-earth complex can be suitably used for luminous ink, organic electroluminescent elements, laser oscillation devices, and the like.

In the rare-earth complex according the present embodiment, $R^1$ is preferably represented by the following general formula (i):

Chem. 5

(i)

where $B^6$ and $B^7$ are each independently an alkylene group, an alkylene group, or an alkynylene group, each of which has a straight chain or a branched chain and which may contain at least one atom selected from the group consisting of O and N, or alternatively —O— or a bonding hand, and $A^{10}$ and $A^{11}$ are each independently an alicyclic hydrocarbon group, an aromatic hydrocarbon group, or a heterocyclic group.

The Ln is a rare earth atom. Since rare earth atoms have nearly same ion radii, Ln is not particularly limited in its type of rare earth atom as long as it is a rare earth atom. In the present embodiment, it is particularly preferable that Ln(III) is $Eu^{3+}$, $Sm^{3+}$, $Tb^{3+}$, $Yb^{3+}$, $Nd^{3+}$, $Ce^{3+}$, $Dy^{3+}$, $Er^{3+}$, $Pr^{3+}$, or $Tm^{3+}$.

The alicyclic hydrocarbon group of $A^1$-$A^9$, $R^2$-$R^5$, $X^1$, $X^2$, and Y is not particularly limited as long as it is a group, other than an aromatic compound, containing a ring structure in which carbon atoms are linked together in a ring state. The ring structure may be monocyclic or polycyclic. The alicyclic hydrocarbon group preferably has a carbon number in a range of 3 to 20, more preferably in a range of 4 to 11. Specific examples of the alicyclic hydrocarbon are, for example, cycloalkanes such as cyclopentane, cyclohexane, methyl cyclohexane, and dicyclohexane, and cycloalkenes such as cyclohexene and bicycloheptene.

The aromatic hydrocarbon group having a condensation polycyclic structure, as $A^1$, is not particularly limited as long as it is a group containing a polycyclic hydrocarbon having aromatic properties. The aromatic hydrocarbon group preferably has a carbon number in a range of 9 to 30, more preferably in a range of 9 to 20. Examples of the aromatic hydrocarbon include, indene, naphthalene, anthracene, phenanthrene, fluorene, biphenylene, naphthacene, and pyrene.

The aromatic hydrocarbon group of $A^2$-$A^9$, $R^2$-$R^5$, $X^1$, $X^2$, and Y is not particularly limited as long as it is a group containing a cyclic hydrocarbon having aromatic properties, and may be monocyclic or polycyclic. The aromatic hydrocarbon group preferably has a carbon number in a range of 6 to 20, more preferably in a range of 6 to 18, and further preferably in a range of 6 to 10. Examples of the aromatic hydrocarbon are, in addition to those exemplified as the aromatic hydrocarbon group having a condensation polycyclic structure, benzene, biphenyl, and terphenyl.

The heterocyclic group of $A^1$-$A^9$, $R^2$-$R^5$, $X^1$, $X^2$, and Y is not particularly limited as long as it is a group containing a ring structure including at least one hetero atom (for example, N, O, P, S), and the group may or may not have aromatic properties. The ring structure thereof may be monocyclic or polycyclic. The heterocyclic group preferably has a carbon number in a range of 3 to 30, more preferably in a range of 3 to 20.

It is preferable that the heterocycle is monocyclic or is a condensed ring of 2 to 6 rigs, of a five-membered ring or a six membered-ring. Examples of the heterocycle of the five-membered ring are furan, pyrrole, oxazole, isoxazole, thiazole, imidazole, pyrazole, thiophene, bithiophene and the like. Examples of the heterocycle of the six membered-ring are pyridine, pyran, triazine and the like. Examples of the condensed ring of the five-membered ring or six membered-ring are benzofuran, coumarin, benzopyran, carbazole, xanthene, 9-dimethylxanthene, quinoline, dibenzofuran and the like. However, these are not limited to the above examples.

The alkenylene group of $A^1$-$A^9$ is not particularly limited as long as it has at least one unsaturated bond in a carbon chain that links together carbon atoms having a free valence, and may be of a straight chain or a branched chain. Moreover, at least one or more groups selected from the above-described group consisting of alicyclic hydrocarbon groups, aromatic hydrocarbon groups, and heterocyclic groups, may be substituted. The alkylene group preferably has a carbon number in a range of 2 to 30, more preferably in a range of 2 to 20.

The expression of "has at least one unsaturated bond in a carbon chain that links together carbon atoms having a free valence" in the present specification specifically means to have at least one unsaturated bond in a carbon chain which links together carbon atoms having a free valence at a shortest distance. For example, —CH=CH—CH$_2$— falls under this definition, whereas —CH(CH=CH$_2$)— does not fall under this definition.

The alkynylene group of $A^1$-$A^9$ is not particularly limited as long as it has one or more unsaturated bonds in a carbon chain that links together carbon atoms having a free valence, and may be of a straight chain or a branched chain. Moreover, the alkynylene group may have at least one or more groups selected from the above-described group consisting of alicyclic hydrocarbon groups, aromatic hydrocarbon groups, and heterocyclic groups be substituted. The alkynylene group preferably has a carbon number in a range of 2 to 30, more preferably in a range of 2 to 20.

It is preferable that the alkylene group and the alkynylene group of $B^1$-$B^5$ have a carbon number in a range of 1 to 20, more preferably have a carbon number in a range of 1 to 8. These groups also may contain at least one atom selected from the group consisting of O and N; for example, the groups may have a bond of ether, ester, ketone, —NHCO—, or the like.

The alkyl group of $R^2$-$R^5$, $X^1$, $X^2$, and Y preferably has a carbon number in a range of 1 to 20, and more preferably has a carbon number in a range of 1 to 8. The alkenyl group and alkynyl group of $R^2$-$R^5$ preferably has a carbon number in a range of 2 to 20, and more preferably has a carbon number in a range of 2 to 8.

In the present embodiment, at least one of $R^2$, $R^3$, $R^4$, and $R^5$ is preferably an alkyl group, an alkenyl group, or an alkynyl group which has a branched chain, and is more preferably an alkyl group having a branched chain. This allows for further improving the luminous efficiency.

It is preferable that the group having a straight chain or a branched chain and containing no hydrogen atom in $X^1$, $X^2$, and Y, has a carbon number in a range of 1 to 20. Examples thereof are a perhalogenated alkyl group, alkenyl group, alkynyl group, cycloalkyl group, or cycloalkenyl group, aromatic group, heteroaromatic group, or aralkyl group. However, it is not limited to these groups. The group may be an ether, ester, or ketone in which one or more of —O— or the like intervenes any C—C bond. Moreover, one or more of halogen atoms bonding to an aromatic ring of the perhalogenated aromatic group, perhalogenated heteroaromatic group, or perhalogenated aralkyl group, may be substituted by a substituent containing no hydrogen atom (for example, cyano, nitro, nitroso, $C_1$-$C_4$ perhalogenated alkoxy, $C_2$-$C_5$ perhalogenated alkoxy carbonyl, $C_2$-$C_{20}$ perhalogenated alkylcarbonyloxy).

It is preferable that the group having a straight chain or a branched chain and containing no hydrogen atom is a perfluorinated alkyl group or a perfluorinated alkenyl group, is further preferable that its carbon number is in a range of 1 to 4, and is most preferably $CF_3$.

In a case where Ln is Eu, Sm, Nd, Yb, Er, Pr, or Dy, it is preferable that $X^1$ and $X^2$ are each independently a group having a $C_1$ to $C_{20}$ straight chain or a $C_1$ to $C_{20}$ branched chain and which contains no hydrogen atom.

On the other hand, in a case where Ln is Tb, $X^1$ and $X^2$ are preferably an alkyl group having a straight chain or a branched chain and which contains a hydrogen atom, or alternatively are an alicyclic hydrocarbon group, an aromatic hydrocarbon group, or a heterocyclic group; $X^1$ and $X^2$ are further preferably an alkyl group having a carbon number in a range of 1 to 4, and is most preferably $CH_3$.

It is preferable that the alkylene group, the alkylene group and the alkynylene group in formula (i) is a $C_1$-$C_5$ alkylene group, a $C_1$-$C_5$ alkylene group, or a $C_1$-$C_5$ alkynylene group. It is more preferable that $B^6$ is —O— and $B^7$ is a $C_1$-$C_5$ alkylene group which may contain at least one atom selected from the group consisting of O and N.

It is preferable that $A^{10}$ and $A^{11}$ in formula (i) are each independently a $C_3$-$C_{10}$ alicyclic hydrocarbon group, a $C_6$-$C_{10}$ aromatic hydrocarbon group or a $C_3$-$C_{10}$ heterocyclic group, is more preferably the $C^6$-$C^{10}$ aromatic hydrocarbon group, and is further preferably a group consisting of benzene.

Specific examples of a phosphine oxide bidentate ligand (n number of ligand(s) coordinated to Ln(III) in general formula (I)) used in the rare-earth complex according to the present embodiment are ligands as exemplified below.

Chem. 6

-continued

-continued

-continued

As described later, the ligand(s) can easily be synthesized by oxidizing a commercially available phosphine compound. Since the phosphine compound is relatively cheap, the rare-earth complex according to the present embodiment may serve advantageously at a time when the rare-earth complex is applied into industrial use.

Although Eu(hfa)$_3$ (BIPHEPO) disclosed in Non Patent Literature 1 (Nakamura K. et al. J. Phys. Chem. A, Vol. 111, No. 16, 3029-3037 (2007)) shows excellent emission properties, in order to synthesize a ligand of BIPHEPO, it is necessary to use expensive base material.

A person skilled in the art who read this specification would easily understand that each of the substituents in a rare-earth complex can be appropriately selected in a range in which a coordination of the phosphine oxide, bidentate ligand to the rare earth metal is not hindered.

As described above, the rare-earth complex according to the present invention, by having the foregoing structure, shows excellent emission properties. Such configuration is an original configuration found out as a result of originality and creativity of the inventors of the present invention.

[II] Production Method of Rare-Earth Complex

The rare-earth complex described above can be synthesized by reacting two types of ligands with a rare earth metal salt, according to a method disclosed in Non Patent Literature 1 (Nakamura K. et al. J. Phys. Chem. A, Vol. 111, No. 16, 3029-3037 (2007)).

The phosphine oxide bidentate ligand described above can be synthesized by, for example, oxidizing a corresponding phosphine compound with hydrogen peroxide or the like.

The following commercially available compounds may be exemplified as a preferable phosphine compound.

Chem. 7

Organic phosphorus compounds are generally stable, and it is easy to synthesize phosphine oxide. Accordingly, a person skilled in the art would be able to synthesize phosphine compounds other than the above, as appropriate.

As to a diketone bidentate ligand (m number of ligand(s) coordinated to Ln(III) in general formula (I)), a person skilled in the art would be able to synthesize this in accordance with Patent Literature 2 (Tokukai, No. 2000-63682 A) and Patent Literature 3 (Tokukai, No. 2003-81986 A), as appropriate.

[III] Luminous Material

The luminous material according to the present embodiment contains the rare-earth complex described above. The luminous material is not particularly limited as long as the luminous material contains the rare-earth complex.

In one embodiment, the luminous material is a composition in which nanocrystals of the rare-earth complex are contained in a dispersed state. In another embodiment, the luminous material according to the present invention is a composition in which nanocrystals of the rare-earth complex are contained in a suspended state. Such compositions may contain solely one type of the rare-earth complex or may contain a plurality of types in combination. By use of the rare-earth complex as nano crystals, the luminous material becomes more difficult to be affected by a medium, and thus the emission properties of the rare-earth complex is maintained. Since the rare-earth complex in the crystal state cannot be easily affected by oxygen or water, it is possible to attain a high durability.

If the rare-earth complex is used as nano crystals, it is preferable that its crystal size is not more than 200 nm.

The content of the rare-earth complex in the luminous material according to the present embodiment is not particularly limited, and can be set as appropriate in accordance with specific purposes or types of media.

The dispersion medium used for the luminous material is not particularly limited, and a preferable medium is selected as appropriate depending on its use. Examples of the desirable medium encompass resin, inorganic material, organic-inorganic hybrid material, and like material.

Examples of the resin encompass polyimide resin, polyamide resin, polymethyl methacrylic resin, polyacrylate, polystyrene resin, polyethylenenaphthalate resin, polyester resin, polyurethane, polycarbonate resin, epoxy resin, polyethylene terephthalate resin, vinyl chloride resin, vinylidene chloride resin, acrylonitrile butadiene styrene (ABS) resin, acrylonitrile styrene (AS) resin, cycloolefin resin, siloxane polymer and these halides or deuterides. The resin may be used solely or a plurality of two or more types may be used in combination. An example of the inorganic material is glass or the like prepared by a sol-gel method.

Furthermore, the luminous material according to the present embodiment may further be added with an additive for providing a specific function to the luminous material, in accordance with its use or the like. For example, additives such as an antioxidant, an inorganic filler, a stabilizer, an antistatic agent, dye, a pigment, a fire retardant, an inorganic filler, and an elastomer for improving shock-proof properties are examples of the additives. Additives such as a lubricant may also be added in order to improve processability of the luminous material according to the present embodiment. In a case where a cast film is to be formed by casting the luminous material according to the present embodiment, a leveling agent may be added to the luminous material.

Examples of the antioxidant encompass the followings: 2,6-di-t-butyl-4-methylphenol, 2,2'-dioxy-3,3'-di-t-butyl-5,5'-dimethylphenylmethane, tetrakis[methylene-3-(3,5-di-t-butyl-4-hydroxyphenyl) propionate]methane, 1,1,3-tris(2-methyl-4-hydroxy-5-t-buthylphenyl)butane, 1,3,5-trimethyl-2,4,6-tris (3,5-di-t-butyl-4-hydroxybenzyl-benzene), stearyl-β-(3,5-di-t-butyl-4-hydroxyphenyl)propionate, 2,2'-dioxy-3,3'-di-t-butyl-5,5'-diethylphenylmethane, 3,9-bis[1,1-dimethyl-2-[β-(3-t-butyl-4-hydroxy-5-methylphenyl) propionyloxy]ethyl], 2,4,8,10-tetraoxyspiro[5,5]undecane, tris (2,4-di-t-buthylphenyl) phosphite, cyclic-neopentane-tetrailbis(2,4-di-t-butylphenyl)phosphite, cyclic-neopentane-tetrailbis(2,6-di-t-butyl-4-methylphenyl) phosphite, 2,2-methylene bis(4,6-di-t-butylphenyl)octyl phosphite.

Examples of the inorganic filler encompass the followings: calcium carbonates, carbon fibers, and metal oxides.

Examples of the leveling agent includes the following: a fluoro nonionic surface active agent, a special acrylic resin leveling agent, and a silicone leveling agent.

The luminous material according to the present embodiment is not particularly limited in its form, and for example forms such as plate, powder, grain, granule, paste, liquid, and emulsion are possible examples of the form of the luminous material. However, since the luminous efficiency improves by the luminous material being present in its crystalline state, it is preferable that the luminous material is in either the plate, powder, grain or granule form.

The production method of the luminous material according to the present embodiment is not particularly limited, and a preferable method is selected as appropriate in accordance with a composition, shape, use, and the like of the luminous material. For instance, in a case where the luminous material is powder, the luminous material can be produced by (i) mixing the rare-earth complex, the medium, and the other additives exemplified above as necessary with a 2-axis extruding machine, Brabender, roll kneader, etc., and (ii) either using an extruder to form the luminous material into a pellet or further crushing this pellet with a crushing machine to make the pellet into powder.

In another embodiment, the luminous material according to the present invention may be of a form of a carrier which holds the nano crystals of the rare-earth complex on its surface. Just one type of the rare-earth complex may be held on such a carrier, or a plurality of types of the rare-earth complexes may be held in combination. The quantity of the rare-earth complex on which the luminous material according to the present embodiment is held is not particularly limited, and the quantity is set as appropriate in accordance with a specific use and type of the carrier.

The production method of the luminous material according to the present embodiment is not particularly limited. For example, the luminous material can be produced by (i) casting a dispersion or a suspension of the luminous material on a carrier (polymer or substrate), and (ii) removing the medium from a formed solution layer. How the dispersion or suspension is cast on the carrier is not particularly limited.

The luminous material can also be produced by forming, on the surface of the carrier, a film of the luminous material according to the present embodiment. The film of the luminous material can be formed on the surface of the carrier by employing a conventionally known method (e.g., a wet process such as a brush coating method, an immersion application method, a spray coating method, a plate coating method, a spinner coating method, a bead coating method, and a curtain coating method; or a film forming method such as gravure printing, screen printing, offset printing, or anastatic printing).

The carrier used for the luminous material according to the present embodiment is not particularly limited, and a preferable carrier is selected as appropriate depending on its use. Examples of a preferable carrier are, for example, the resins, inorganic material, and organic-inorganic hybrid material described above.

[IV] Light Emitting Device

A light emitting device according to the present embodiment includes a light source and the luminous material described above. In the light emitting device, the luminous material described above is irradiated with light emitted from a light source, which excites the rare-earth complex in the luminous material and emits light. As a result, the light emitting device according to the present embodiment shows outstanding emission properties.

A conventionally known light source may be employed as the light source, and examples thereof include a heavy hydrogen lamp, a tungsten lamp, an ultraviolet LED, a xenon lamp, a mercury lamp, a blacklight, a halogen lamp, a short wavelength semiconductor laser and the like.

As described above, in the rare-earth complex according to the present invention, it is preferable that $R^1$ is represented by the following general formula (i):

Chem. 8

(i)

where $B^6$ and $B^7$ are each independently an alkylene group, an alkylene group or an alkynylene group, each of which has a straight chain or a branched chain and which may contain at least one atom selected from the group consisting of O and N, or alternatively —O— or a bonding hand, and $A^{10}$ and $A^{11}$ are each independently an alicyclic hydrocarbon group, an aromatic hydrocarbon group, or a heterocyclic group.

According to the arrangement, the foregoing structure allows for showing a higher luminous efficiency. With the foregoing structure, a change in configuration in the phosphine oxide bidentate ligand is more restricted. Hence, it is assumed that the configuration is more contributive to the emission properties.

In the rare-earth complex according to the present invention, it is preferable that $B^6$ and $B^7$ are each independently a $C_1$-$C_5$ alkylene group, a $C_1$-$C_5$ alkylene group or a $C_1$-$C_5$ alkynylene group, each of which has a straight chain or a branched chain and which may contain at least one atom selected from the group consisting of O and N, or alternatively, —O— or a bonding hand.

Furthermore, in the rare-earth complex according to the present invention, it is preferable that $B^6$ is —O— and $B^7$ is a $C_1$-$C_5$ alkylene group which may contain at least one atom selected from the group consisting of O and N, and $A^{10}$ and $A^{11}$ are each independently a $C_6$-$C_{10}$ aromatic hydrocarbon group.

According to the arrangement, the foregoing structure allows for showing a higher luminous efficiency. With the foregoing structure, a change in configuration in the phosphine oxide bidentate ligand is more restricted. Hence, it is assumed that the configuration is more contributive to the emission properties.

In the rare-earth complex according to the present invention, it is preferable that $R^1$ is -$A^3$-$B^3$-$A^4$-, and $B^3$ is —O—.

According to the arrangement, the foregoing structure allows for obtaining a higher luminous efficiency.

In the rare-earth complex according to the present invention, it is preferable that Ln is Eu, Sm, Nd, Yb, Er, Pr, or Dy, and $X^1$ and $X^2$ are each independently a group having a $C_1$-$C_{20}$ straight chain or a $C_1$-$C_{20}$ branched chain and which contains no hydrogen atom.

With the arrangement, the luminous efficiency is increased more. The luminous efficiency is considered as being increased more due to the fact that since $X^1$ and $X^2$ do not contain a hydrogen atom in the arrangement, a molecular vibration is small, and as a result electrons excited by molecular vibration is prevented from being deactivated.

In the rare-earth complex according to the present invention, it is preferable that Ln is Tb, and, $X^1$ and $X^2$ are each independently an alkyl group having a straight chain or a branched chain and which contains a hydrogen atom, or alternatively, an alicyclic hydrocarbon group, an aromatic hydrocarbon group, or a heterocyclic group.

With the arrangement, the luminous efficiency increases more. The arrangement allows for preventing reverse movement of excited energy, thereby allowing for efficiently emitting excited energy. It is thought that as a result, the luminous efficiency is further improved.

In the rare-earth complex according to the present invention, it is preferable that at least one of $R^2$, $R^3$, $R^4$ and $R^5$ is a $C_1$-$C_{20}$ alkyl group, a $C_2$-$C_{20}$ alkynyl group, or a $C_2$-$C_{20}$ alkenyl group, having a branched chain.

According to the arrangement, the foregoing structure allows for the luminous efficiency to increase more.

The present invention is not limited to the description of the embodiments above, but may be altered by a skilled person within the scope of the claims. An embodiment based on a proper combination of technical means disclosed in different embodiments is encompassed in the technical scope of the present invention.

All academic literature and patent literature that have been mentioned in the present specification are incorporated as reference in the present specification.

EXAMPLES

The present invention is explained below in detail based on Examples. However, the present invention is not limited to the following examples. Note that "hexafluoroacetylacetonato" may be hereinafter abbreviated as "hfa".

Unless specified, raw materials and solvents were used as they are in their commercially available state (Nacalai Tesque, Inc., Wako Pure Chemical Industries, Ltd., Tokyo Chemical Industries, Co., Ltd, Aldrich Co.). Identification of each compound was carried out by $^1$H NMR (JEOL, 300 MHz), $^{31}$P NMR (JEOL, 200 MHz), FAB-Mass spectrum (JEOL, JMS-700, MStation), ESI-Mass spectrum (JEOL, JMS-700, MStation), FT-IR measurement (JASCO FT/IR-420), and elementary analysis (Perkin Elmer 240011).

Example 1

Synthesis of (9,9-dimethyl-9H-xanthene-4,5-diyl)bis(diphenylphosphine oxide) (XANTPO) (Compound 2)

Chem. 9

Compound 1 (1.0 g, 1.7 mmol) (purchased from Tokyo Chemical Industries, Co., Ltd.) was melted in $CH_2Cl_2$, and $H_2O_2$ (30%, 4.0 mL) was dropped therein while cooling the mixture at 0° C. This mixture was stirred for 2 hours. A reaction solution was separated by use of $CH_2Cl_2$ and an organic layer was dried with magnesium sulfate. Thereafter, magnesium sulfate was removed by filtration and the solvent was distilled off. An obtained solid was washed with hexane and filtered, which yielded a compound 2 (white powder, 1.06 g, 100%).

IR (ATR) 1190 (st, P=O), 1100-1229 (st, C—O—C) cm$^{-1}$ $^1$H NMR (300 MHz, CDCl$_3$/TMS) δ7.58-7.60 (d, J=6 Hz, 2H), 7.30-7.47 (m, 20H), 6.94-7.00 (t, J=6 Hz, 2H), 6.78-6.85 (m, 2H), 1.69 (s, 6H) ppm.

$^{31}$P NMR (200 MHz, CDCl$_3$, 25° C.) δ33.55 (1P), 30.32 (1P) ppm

FAB-Mass (m/z)=611 [M+H]$^+$.

Synthesis of Eu(hfa)$_3$ (XANTPO) (Compound 3)

Chem. 10

In 20 mL of methanol, 0.20 g (0.33 mmol, 1.0 Eq) of compound 2 and 0.32 g (0.39 mmol, 1.2 Eq) of Eu(hfa)$_3$(H$_2$O)$_2$ were dissolved, and this mixture was heated to reflux for 12 hours at 80° C. After distilling off the methanol under reduced pressure, an obtained solid was washed with chloroform and impurities were removed by filtration. A solvent contained in the filtrate was distilled off under reduced pressure, which yielded a compound 3 (yellowish-white colored crystals, 0.20 g, 44%).

IR (ATR) 1653 (st, C=O), 1137 (st, P=O), 1095-1251 (st, C—O—C and st, C—F) cm$^{-1}$ $^1$H NMR (300 MHz, CDCl$_3$/TMS) δ7.62-7.65 (d), 7.26 (br), 7.04 (br), 6.74 (br), and 1.88 (s) ppm $^{31}$P NMR (200 MHz, acetone-d$_6$, 25° C.) δ−92.12 (2P), −98.86 (2P) ppm ESI-Mass (m/z) [M]$^+$ calcd. for $C_{49}H_{34}EuF_{12}O_7P_2^+$, 1177.081. found, 1177.081

ESI-Mass (m/z) [M-(hfa)]$^+$ calcd. for $C_{88}H_{66}EuF_{12}O_{10}P_4$, 1787.264. Found, 1787.264

Anal. Calcd. for $C_{93}H_{67}EuF_{18}O_{12}P_4 \cdot 1.5CHCl_3$: C, 52.22; H, 3.18. Found: C, 52.11; H, 3.25.

<Evaluation of Emission Properties>

Absorption-spectrum measurement was carried out by use of JASCO V-660, and emission-spectrum measurement was carried out by use of HITACHI F-4500. Heavy acetone solution of $1.0 \times 10^{-2}$ M was prepared and was used for measurement. In order to prevent quenching caused by dissolved oxygen, Ar bubbling was performed for 30 minutes before measurement. The measurement was performed at an excitation wavelength of 465 nm (direct excitation of Eu(III) ion). Quantum yield was calculated by a comparison method using a known Eu(III) complex ($\phi$=0.60 in a heavy acetone solution of Eu(hfa)$_3$ (BIPHEPO), $5.0 \times 10^{-2}$ M).

Eu(hfa)$_3$ (BIPHEPO) was prepared by a method disclosed in Non Patent Literature 1 (Nakamura K. et al., J. Phys. Chem. A, Vol. 111, No. 16, 3029-3037. (2007)).

Figure 1:
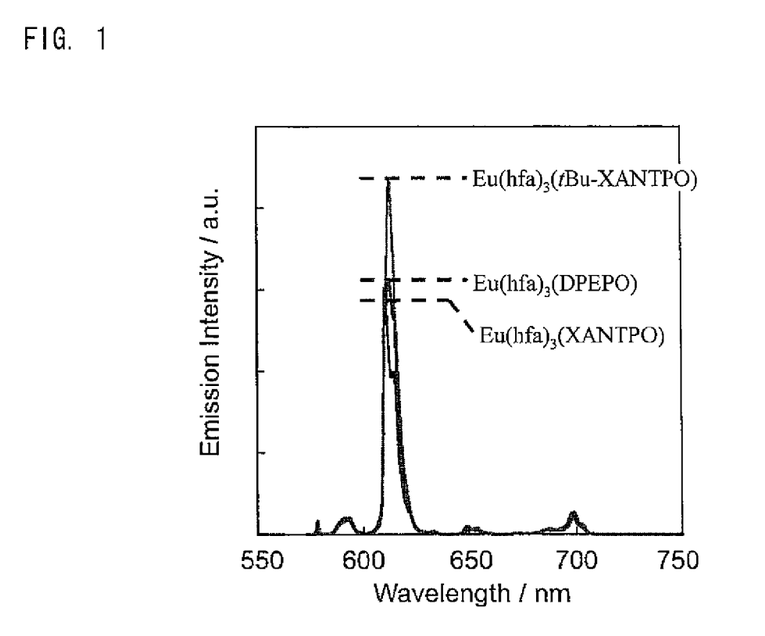
FIG. 1 is a graph illustrating emission spectra of rare-earth complexes prepared in Examples 1 and 2.

FIG. 1 shows an emission spectrum of Eu(hfa)$_3$ (XANTPO), and Table 1 shows its quantum yield $\phi$, its relative emission intensity $I_{rel}$, its emission lifetime $\tau_{obs}$, its radiation kinetic constant $k_r$, and its nonradiation kinetic constant $k_{nr}$. As a result, it was confirmed that Eu(hfa)$_3$ (XANTPO) emits light with a high quantum yield of a same degree as Eu(hfa)$_3$ (BIPHEPO).

Each emission spectrum shown in FIG. 1 was standardized with an emission intensity of 592 nm.

Example 2

Synthesis of (9,9-dimethyl-9H-xanthene-4,5-diyl)bis (di-tert-butylphosphine oxide) (tert-BuXANTPO) (Compound 4)

Chem. 11

Compound 3 (1.0 g, 2.0 mmol) (purchased from Tokyo Chemical Industries, Co., Ltd.) was melted in CH$_2$Cl$_2$, and H$_2$O$_2$ (30%, 4.5 mL) was dropped therein while cooling the mixture at 0° C. This mixture was stirred for 2 hours. The reaction solution was separated with use of CH$_2$Cl$_2$ and an organic layer was dried with magnesium sulfate. Thereafter, magnesium sulfate was removed by filtration and the solvent was distilled off. An obtained solid was washed with hexane and was filtered, which yielded a compound 4 (white powder, 0.97 g, 91%).

IR (ATR) 1180 (st, P=O), 1103-1200 (st, C—O—C) cm$^{-1}$
$^1$H NMR (300 MHz, CDCl$_3$/TMS) $\delta$7.82-7.84 (d, J=6 Hz, 2H), 7.53-7.60 (m, 2H), 7.40-7.46 (m, 2H), 1.67 (s, 6H), 1.35-1.46 (m, 36H) ppm
$^{31}$P NMR (200 MHz, CDCl$_3$, 25° C.) $\delta$69.53 (1P), 58.36 (1P) ppm
FAB-Mass (m/z)=531 [M+H]$^+$.

Synthesis of Eu(hfa)$_3$ (tert-BuXANTPO) (Compound 5)

Chem. 12

In 20 mL of methanol, 0.22 g (0.41 mmol, 1.0 Eq) of compound 4 and 0.40 g (0.49 mmol, 1.2 Eq) of Eu(hfa)$_3$ (H$_2$O)$_2$ were melted, and this mixture was heated to reflux for 12 hours at 80° C. After distilling off the methanol under reduced pressure, an obtained solid was washed with chloroform and impurities were removed by filtration. The solvent contained in the filtrate was distilled off under reduced pressure, thereby obtaining compound 5 (colorless, transparent amorphous state, 0.35 g, 66%).

IR (ATR) 1653 (st, C=O), 1138 (st, P=O), 1098-1249 (st, C—O—C and st, C—F) cm$^{-1}$
$^1$H NMR (300 MHz, CDCl$_3$/TMS) $\delta$7.41 (br, 2H), 7.07 (br, 2H), 6.83 (br, 2H), 1.68 (s, 6H), 1.41-1.46 (d, J=15 Hz, 36H) ppm.
$^{31}$P NMR (200 MHz, acetone-d$_6$, 25° C.) $\delta$68.41 (2P) ppm
ESI-Mass (m/z) [M]$^+$ calcd. for C$_{41}$H$_{50}$EuF$_{12}$O$_7$P$_2$$^+$, 1097.206. found, 1097.206
Anal. Calcd. for C$_{46}$H$_{51}$EuF$_{18}$O$_9$P$_2$: C, 42.38; H, 3.94. Found: C, 42.93; H, 4.00.

<Evaluation of Emission Properties>

The emission properties of Eu(hfa)$_3$ (tert-BuXANTPO) was evaluated by the same method as Example 1. FIG. 1 shows its emission spectrum, and Table 1 shows its quantum yield $\phi$, its relative emission intensity $I_{rel}$, its emission lifetime $\tau_{obs}$, its radiation kinetic constant $k_r$, and its nonradiation kinetic constant $k_{nr}$. As a result, it was confirmed that Eu(hfa)$_3$ (tert-BuXANTPO) emits light with a quantum yield higher than that of Eu(hfa)$_3$ (BIPHEPO). The emission intensity was of a same degree as Eu(hfa)$_3$ (BIPHEPO).

Example 3

Synthesis of bis[(2-diphenylphosphoryl)phenyl]ether (DPEPO) (Compound 9)

Compound 8 (5.0 g, 9.3 mmol) was melted in 100 mL of CH$_2$Cl$_2$, and H$_2$O$_2$ (30%, 4.0 mL, 186 mmol) was dropped therein while the mixture was being ice bathed. This mixture was stirred for 4 hours. The reactant was quenched with distilled water after stirring, and CH$_2$Cl$_2$ extraction was performed 3 times. An organic layer was dried with anhydrous magnesium sulfate, and the solvent was distilled off. An obtained solid was purified by a reprecipitation method with use of hexane, which yielded a compound 9 (white powder, 5.0 g, 94%).

IR (ATR) 1183 (st, P=O), 1070-1226 (st, C—O—C) cm$^{-1}$ $^1$H NMR (300 MHz, CDCl$_3$, 25° C.) δ7.06-7.71 (m, 26H, Ar), 6.02-6.07 (m, 2H, Ar) ppm $^{31}$P NMR (200 MHz, CDCl$_3$, 25° C.) δ26.41 (2P) ppm FAB-Mass (m/z)=571 [M+H]$^+$.

<Composition of Eu(hfa)$_3$ (DPEPO) (Compound 10)>

In methanol, 1 equivalent amount of compound 9 and 1.2 equivalent amounts of Eu(hfa)$_3$(H$_2$O)$_2$ were melted, and this mixture was heated to reflux for 8 hours at 80° C. After distilling off the methanol under reduced pressure, an obtained solid was washed with chloroform and impurities were removed by filtration. A solvent contained in the filtrate was distilled off under reduced pressure, which yielded a yellowish-white colored powder. Recrystallization was carried out with methanol, which yielded a compound 10 (colorless minute block-shaped crystals, 0.62 g, 74%).

IR (ATR) 1653 (st, C=O) and 1135 (st, P=O), 1098-1251 (st, C—O—C and st, C—F) cm$^{-1}$ $^1$H NMR (500 MHz, acetone-d$_6$, 25° C.) δ7.32-7.64 (m, 22H, Ar), 7.10-7.13 (t, J=7.5 Hz, 2H, Ar), 6.90-6.95 (dd, J=7.5 Hz, 2H, Ar), 6.73 (s, 3H, hfa-H), 6.29-6.30 (m, 2H, Ar) ppm $^{31}$P NMR (200 MHz, acetone-d$_6$, 25° C.) δ−113.42 (2P) ppm ESI-Mass (m/z) Calcd. for C$_{46}$H$_{30}$EuF$_{12}$O$_7$P$_2$ [M-(hfa)]$^+$: 1137.049. Found: 1137.049

Anal. Calcd. for C$_{51}$H$_{31}$EuF$_{18}$O$_9$P$_2$: C, 45.59; H, 2.33. Found: C, 45.76; H, 2.11.

<Evaluation of Emission Properties>

The emission properties of Eu(hfa)$_3$ (DPEPO) was evaluated in the same method as Example 1. FIG. 1 shows its emission spectrum, and Table 1 shows its quantum yield φ, its emission lifetime $\tau_{obs}$, its radiation kinetic constant $k_r$, and its nonradiation kinetic constant $k_{nr}$. As a result, it was confirmed that Eu(hfa)$_3$ (DPEPO) emitted light with a quantum yield higher than that of Eu(hfa)$_3$ (BIPHEPO).

As shown in Table 1, the luminous efficiency of Eu(hfa)$_3$ (DPEPO) and Eu(hfa)$_3$ (tert-BuXANTPO) showed values higher than that of Eu(hfa)$_3$ (BIPHEPO) that is known as a rare-earth complex with high luminous efficiency. For this reason, when such a rare-earth complex is used for luminous security ink for example, it is possible to achieve a security ink having high emission abilities and having high functions.

TABLE 1

| Ex. | Complex | Quantum yield φ/% | Emission lifetime $\tau_{obs}$/ms | Radiation kinetic constant $k_r$/s$^{-1}$ | Nonradiation kinetic constant $k_{nr}$/s$^{-1}$ | Relative emission intensity $I_{rel}$ |
|---|---|---|---|---|---|---|
| 1 | Eu(hfa)$_3$ (XANTPO) | 54 | 1.3 | 4.4 × 10$^2$ | 3.6 × 10$^2$ | 18 |
| 2 | Eu(hfa)$_3$ (tert-BuXANTPO) | 71 | 1.2 | 5.5 × 10$^2$ | 2.7 × 10$^2$ | 26 |
| 3 | Eu(hfa)$_3$ (DPEPO) | 72 | 1.5 | 4.7 × 10$^2$ | 1.8 × 10$^2$ | |
| — | Eu(hfa)$_3$ (BIPHEPO) | 60 | 1.3 | 4.6 × 10$^2$ | 3.4 × 10$^2$ | 28 |

Example 4

Synthesis of Sm(hfa)$_3$ (XANTPO) (Compound 6)

Chem. 15

In 30 mL of methanol, 0.50 g (0.85 mmol, 1.0 Eq) of compound 2 and 0.76 g (0.94 mmol, 1.1 Eq) of Sm(hfa)$_3$ (H$_2$O)$_2$ were melted, and this mixture was heated to reflux for 12 hours at 80° C. After distilling off the methanol under reduced pressure, the obtained solid was washed with chloroform and impurities were removed by filtration. The solvent contained in the filtrate was distilled off under reduced pressure, which yielded a compound 6 (white powder, 0.79 g, 68%).

IR (ATR) 1653 (st, C=O), 1138 (st, P=O), 1100-1252 (st, C—O—C and st, C—F) cm$^{-1}$ $^1$H NMR (300 MHz, CDCl$_3$/TMS) δ6.41-7.94 (m), 1.49-1.71 (t, J=33 Hz) ppm.

$^1$H NMR (500 MHz, acetone-d$_6$, 25° C.) δ5.81-8.09 (m), 1.67 (s, Me), 1.52 (s, Me) ppm $^{31}$P NMR (200 MHz, acetone-d$_6$, 25° C.) δ33.03 (2P), 32.80 (2P) ppm ESI-Mass (m/z) [M]$^+$ calcd. for C$_{49}$H$_{34}$F$_{12}$O$_7$P$_2$Sm$^+$, 1176.079. found, 1176.081

ESI-Mass (m/z) [M-(hfa)]$^+$ calcd. for C$_{88}$H$_{66}$SmF$_{12}$O$_{10}$P$_4$, 1786.257. Found, 1786.261

Anal. Calcd. for C$_{93}$H$_{78}$SmF$_1$O$_{15}$P$_4$: C, 55.99; H, 3.94. Found: C, 55.54; H, 3.53.

<Evaluation of Emission Properties>

For the emission-spectrum measurement, HITACHI F-4500 was used. Heavy acetone solution of 1.0×10$^{-2}$ M was prepared and was used for measurement. In order to prevent quenching caused by dissolved oxygen, Ar bubbling was performed for 30 minutes before measurement. The measurement was performed at an excitation wavelength of 481 nm (direct excitation of Sm(III) ion). Quantum yield was calculated by a comparison method using known Sm(III) complex (φ=0.031 in heavy DMSO solution of Sm(hfa)$_3$(H$_2$O)$_2$ and 1.0×10$^{-1}$ M).

Figure 2:
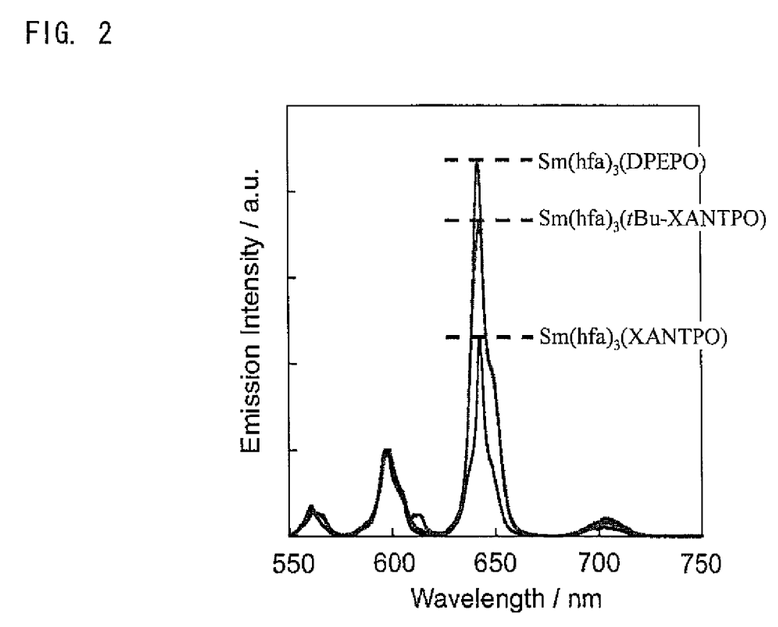
FIG. 2 is a graph illustrating emission spectra of rare-earth complexes prepared in Examples 3 and 4.

FIG. 2 shows the emission spectrum of Sm(hfa)$_3$ (XANTPO). As a result, it was confirmed that Sm(hfa)$_3$ (XANTPO) emits an extremely strong light in the vicinity of 650 nm which is close to a pure red color.

Table 2 shows its quantum yield φ, its emission lifetime $\tau_{obs}$, its radiation kinetic constant $k_r$, and its nonradiation kinetic constant $k_{nr}$. As a result, it was confirmed that Sm(hfa)$_3$ (XANTPO) emits light with a quantum yield higher than that of Sm(hfa)$_3$(H$_2$O)$_2$.

Each emission spectrum shown in FIG. 1 was standardized with an emission intensity of 598 nm.

Example 5

Synthesis of Sm(hfa)₃ (tert-BuXANTPO) (Compound 7)

Chem. 16

In 20 mL of methanol, 0.30 g (0.57 mmol, 1.0 Eq) of compound 4 and 0.55 g (0.68 mmol, 1.2 Eq) of Sm(hfa)₃(H₂O)₂ were melted, and this mixture was heated to reflux for 12 hours at 80° C. After distilling off the methanol under reduced pressure, an obtained solid was washed with chloroform and impurities were removed by filtration. A solvent in the filtrate was distilled under reduced pressure, which yielded a compound 7 (white powder, 0.39 g, 53%).

IR (ATR) 1653 (st, C=O), 1137 (st, P=O), 1100-1252 (st, C—O—C and st, C—F) cm⁻¹

¹H NMR (300 MHz, CDCl₃/TMS) δ7.82 (m), 7.26-7.60 (m), 1.26-1.79 (m) ppm.

¹H NMR (500 MHz, acetone-d₆, 25° C.) δ8.06-8.08 (d, J=7.5 Hz, 2H, Ar), 7.73-7.77 (m, 2H, Ar), 7.50-7.53 (t, J=7.5 Hz, 2H, Ar), 6.73 (s, 3H, hfa-H), 1.83 (s, 6H, 2Me), 0.52-0.55 (d, J=15 Hz, 36H, 4 tBu) ppm ³¹P NMR (200 MHz, acetone-d₆, 25° C.) δ62.37 (2P) ppm ESI-Mass (m/z) [M]⁺ calcd. for C₄₁H₅₀F₁₂O₇P₂Sm⁺, 1096.204. found, 1096.200

Anal. Calcd. for C₄₆H₅₁SmF₁₈O₉P₂: C, 42.43; H, 3.95. Found: C, 42.68; H, 3.71.

<Evaluation of Emission Properties>

The emission properties of Sm(hfa)₃ (tert-BuXANTPO) were evaluated in the same method as Example 4. FIG. 2 shows the emission spectrum of Sm(hfa)₃ (tert-BuX-ANTPO). As a result, it was confirmed that an extremely strong light was emitted around 650 nm that is close to a pure red color.

Table 2 shows its quantum yield φ, its emission lifetime τ$_{obs}$, its radiation kinetic constant k$_r$, and its nonradiation kinetic constant k$_{nr}$. As a result, it was confirmed that Sm(hfa)₃ (tert-BuXANTPO) emits light with a quantum yield of a same degree as Sm(hfa)₃(H₂O)₂.

Example 6

Synthesis of Sm(hfa)₃ (DPEPO) (Compound 11)

Chem. 17

In methanol, 1 equivalent amount of compound 9 and 1.2 equivalent amounts of Sm(hfa)₃(H₂O)₂ were melted, and this mixture was heated to reflux for 8 hours at 80° C. After distilling off the methanol under reduced pressure, an obtained solid was washed with chloroform and impurities were removed by filtration. A solvent contained in the filtrate was distilled off under reduced pressure, which yielded a yellowish-white colored powder. Recrystallization was carried out with methanol, which yielded a compound 11 (colorless minute block-form crystals, 0.66 g, 79%).

IR (ATR) 1653 (st, C=O), 1134 (st, P=O), 1098-1250 cm$^{-1}$ $^1$H NMR (500 MHz, acetone-d$_6$, 25° C.) δ7.32-7.64 (m, 22H, Ar), 7.10-7.13 (t, J=7.5 Hz, 2H, Ar), 6.90-6.95 (dd, J=7.5 Hz, 2H, Ar), 6.73 (s, 3H, hfa-H), 6.29-6.30 (m, 2H, Ar) ppm $^{31}$P NMR (200 MHz, acetone-d$_6$, 25° C.) δ29.17 (2P) ppm ESI-Mass (m/z) Calcd. for C$_{46}$H$_{30}$SmF$_{12}$O$_7$P$_2$ [M-(hfa)]$^+$: 1136.048. Found: 1136.044

Anal. Calcd. for C$_{51}$H$_{31}$SmF$_{18}$O$_9$P$_2$: C, 45.64; H, 2.33. Found: C, 45.54; H, 2.18.

<Evaluation of Emission Properties>

The emission properties of Sm(hfa)$_3$ (DPEPO) were evaluated in the same method as Example 4. FIG. 2 shows the emission spectrum of Sm(hfa)$_3$ (DPEPO). As a result, it was confirmed that very strong emission was observed around 650 nm that is close to a more pure red.

Table 2 shows its quantum yield φ, its emission lifetime τ$_{obs}$, its radiation kinetic constant k$_r$, and its nonradiation kinetic constant k$_{nr}$. As a result, it was confirmed that Sm(hfa)$_3$ (DPEPO) emits light with a quantum yield higher than that of Sm(hfa)$_3$(H$_2$O)$_2$.

Although the quantum yield of Sm complex obtained in Examples 4 to 6 is in a range of 2.4 to 5.0%, this is an extremely high value for a Sm complex (a quantum yield of 5.0% is the world's maximum value among Sm complexes). The Sm complex is an ideal substance as luminous material for use in display since the Sm complex emits a deeper red light than the Eu complex. However, it is generally difficult to have the Sm complex emit light, and in most cases, the quantum yield of the Sm complex was not more than 1%. Namely, the Sm complex obtained in Examples 4 to 6 show extremely strong light emission as compared to the conventionally-reported Sm complex.

TABLE 2

| Ex. | Complex | Quantum yield φ/% | Emission lifetime τ$_{obs}$/ms | Radiation kinetic constant k$_r$/s$^{-1}$ | Nonradiation kinetic constant k$_{nr}$/s$^{-1}$ |
|---|---|---|---|---|---|
| 4 | Sm(hfa)$_3$ (XANTPO) | 3.8 | 0.35 | 1.1 × 10$^2$ | 2.8 × 10$^2$ |
| 5 | Sm(hfa)$_3$ (tBu-XANTPO) | 2.4 | 0.15 | 1.6 × 10$^2$ | 6.5 × 10$^2$ |
| 6 | Sm(hfa)$_3$ (DPEPO) | 5.0 | 0.28 | 1.8 × 10$^2$ | 3.3 × 10$^2$ |

Industrial Applicability

A rare-earth complex according to the present invention has excellent emission properties. Therefore, the rare-earth complex can be suitably used in luminous ink and/or organic electroluminescence elements.

The invention claimed is:

1. A rare-earth complex represented by the following general formula (I):

Chem. 1 wherein
Ln is Eu or Sm, and
R$^1$ is the following general formula (i):

Chem. 2 where B$^6$ and B$^7$ are each independently an alkylene group or alkynylene group, each of which having a straight chain or a branched chain and which may contain at least one atom selected from the group consisting of O and N, or alternatively, —O—, and
A$^{10}$ and A$^{11}$ are each independently an alicyclic hydrocarbon group, an aromatic hydrocarbon group, or a heterocyclic group,
(a) wherein when Ln is Eu, at least one of R$^2$, R$^3$, R$^4$, and R$^5$ is a C$_1$ - C$_{20}$ alkyl group, a C$_2$ - C$_{20}$ alkenyl group, or a C$_2$ - C$_{20}$ alkynyl group, having a branched chain;
(b) wherein when Ln is Sm, R$^2$, R$^3$, R$^4$, and R$^5$ each independently being an alkyl group, alkenyl group or alkynyl group each having a straight chain or a branched chain, or alternatively an alicyclic hydrocarbon group, an aromatic hydrocarbon group, or a heterocyclic group;
X$^1$ and X$^2$ each independently being perhalogenated alkyl groups,
Y being hydrogen, heavy hydrogen, a halogen group, a hydroxyl group, a sulfonic group, a carbonyl group, a nitro group, a cyano group, an amino group, an alkyl group having a straight chain or a branched chain, or alternatively, an alicyclic hydrocarbon group, an aromatic hydrocarbon group, a heterocyclic group, or a group made of a straight chain or a branched chain including no hydrogen atom, and
n being 1 or 2; m being 2, 3, or 4.

2. Luminous material comprising the rare-earth complex as set forth in claim 1.

3. A light emitting device comprising:
a light source; and
the luminous material as set forth in claim 2.

4. The rare-earth complex according claim 1, wherein Ln is Sm.

* * * * *